(12) United States Patent
Webster et al.

(10) Patent No.: US 10,130,415 B2
(45) Date of Patent: Nov. 20, 2018

(54) CIRCUMFERENTIAL ELECTRODE ARRAY FOR TISSUE ABLATION

(75) Inventors: John G. Webster, Madison, WI (US); Dieter Haemmerich, Charleston, SC (US); James Arthur Will, Columbus, WI (US); David Mahvi, Middleton, WI (US); Ann O'Rourke, Madison, WI (US); David James Schutt, Charleston, SC (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2673 days.

(21) Appl. No.: 12/072,208

(22) Filed: Feb. 25, 2008

(65) Prior Publication Data

US 2009/0036882 A1 Feb. 5, 2009

Related U.S. Application Data

(63) Continuation-in-part of application No. 10/945,380, filed on Sep. 20, 2004, now Pat. No. 7,367,974.

(60) Provisional application No. 60/946,657, filed on Jun. 27, 2007.

(51) Int. Cl.
| | | |
|---|---|---|
| A61B 18/18 | (2006.01) | |
| A61B 18/14 | (2006.01) | |
| A61B 17/00 | (2006.01) | |
| A61B 18/00 | (2006.01) | |
| A61B 18/12 | (2006.01) | |

(52) U.S. Cl.
CPC ............ *A61B 18/1477* (2013.01); *A61B 2017/00017* (2013.01); *A61B 2017/00022* (2013.01); *A61B 2017/00026* (2013.01); *A61B 2018/0075* (2013.01); *A61B 2018/00654* (2013.01); *A61B 2018/00726* (2013.01); *A61B 2018/00755* (2013.01); *A61B 2018/00791* (2013.01); *A61B 2018/00797* (2013.01); *A61B 2018/00827* (2013.01); *A61B 2018/00875* (2013.01); *A61B 2018/124* (2013.01); *A61B 2018/143* (2013.01); *A61B 2018/1432* (2013.01); *A61B 2018/1467* (2013.01); *A61B 2560/0418* (2013.01)

(58) Field of Classification Search
CPC ......... A61B 18/14–18/1492; A61B 2560/0418
USPC ....................................... 606/33–51
See application file for complete search history.

(56) References Cited

U.S. PATENT DOCUMENTS

| | | | |
|---|---|---|---|
| 5,196,008 A | | 3/1993 | Kuenecke et al. |
| 5,536,267 A | * | 7/1996 | Edwards ............ A61B 18/1477 606/48 |
| 5,620,481 A | * | 4/1997 | Desai et al. ..................... 606/42 |
| 5,993,434 A | * | 11/1999 | Dev ...................... A61N 1/325 604/20 |
| 6,050,992 A | * | 4/2000 | Nichols ......................... 606/41 |
| 6,068,650 A | * | 5/2000 | Hofmann et al. ................ 607/2 |
| 6,080,150 A | | 6/2000 | Gough |
| 6,379,349 B1 | | 4/2002 | Müller et al. |
| 6,524,308 B1 | | 2/2003 | Muller et al. |

(Continued)

*Primary Examiner* — David Shay
(74) *Attorney, Agent, or Firm* — Boyle Fredrickson S.C.

(57) ABSTRACT

An electrode array supports multiple electrodes and energizes them so that adjacent electrodes do not have the same polarity. In one embodiment, the electrodes are held about a circumference outside and surrounding a tumor and opposed electrodes are energized in a round robin fashion to promote current flow through the center of the tumor from a variety of angles.

18 Claims, 9 Drawing Sheets

(56) References Cited

U.S. PATENT DOCUMENTS

| | | | |
|---|---|---|---|
| 6,549,810 B1* | 4/2003 | Leonard | A61N 1/0551 607/115 |
| 6,818,000 B2 | 11/2004 | Muller et al. | |
| 7,008,421 B2 | 3/2006 | Daniel et al. | |
| 7,278,991 B2* | 10/2007 | Morris | A61B 18/1477 606/41 |
| 2002/0111615 A1* | 8/2002 | Cosman et al. | 606/41 |
| 2002/0120261 A1 | 8/2002 | Morris et al. | |
| 2004/0181216 A1 | 9/2004 | Kelly et al. | |
| 2006/0015095 A1 | 1/2006 | Desinger et al. | |
| 2006/0293731 A1* | 12/2006 | Rubinsky et al. | 607/98 |

* cited by examiner

FIG. 21C

CIRCUMFERENTIAL ELECTRODE ARRAY FOR TISSUE ABLATION

CROSS-REFERENCE TO RELATED APPLICATIONS

This application is a continuation-in-part of U.S. application Ser. No. 10/945,380 filed Sep. 20, 2004 and entitled: "Electrode Array for Tissue Ablation", hereby incorporated by reference. This application claims the benefit of U.S. provisional application 60/946,657 filed Jun. 27, 2007, hereby incorporated by reference.

STATEMENT REGARDING FEDERALLY SPONSORED RESEARCH OR DEVELOPMENT

This invention was made with United States Government Support awarded by the following agency:
NIH DK058839, HL56143.
The United States government has certain rights in this invention.

BACKGROUND OF THE INVENTION

The present invention relates to radiofrequency (RF) ablation of tumors and, in particular, to an apparatus and method for safely ablating large tumors, for example, within organs such as the liver.

Malignant liver tumors are a substantial problem in the United States and worldwide. Virtually all patients who succumb to colorectal cancer have evidence of metastatic tumors in the liver at the time of death resulting from the filtering and scavenging mechanism of the liver.

Large studies demonstrate a five-year survival advantage in 33% of the cases in which all macroscopic tumors of liver-only metastatic colorectal carcinomas are removed. In contrast, treatment by chemotherapy alone results in approximately zero percent, five-year survival rates.

Nevertheless, surgical resection or removal of the tumors is not always possible. Liver lesions, located deep in the hepatic parenchyma are usually not amenable to wedge resection and thus require a segmentectomy or lobectomy for complete removal. Resection of multiple, deep lesions may require the loss of an unacceptable amount of hepatic parenchyma. Extensive hepatic resections increase postoperative morbidity and mortality, including post-operative hepatic failure. In addition, the need for transfusion during hepatic resection increases the tumor recurrence rate, probably due to poorly understood immunological mechanisms.

In cases where surgery is not practical, RF ablation for tumor destruction may be preferred, yet it can be difficult to ablate large tumors reliably, especially in perivascular tissue and at tumor margins. Although ablation induced temperatures above 60° centigrade are almost instantaneously cytotoxic, it takes four to six minutes for cells to undergo irreversible change when exposed to 50° centigrade. It is difficult to provide uniformly high temperatures throughout a large tumor volume, particularly near blood vessels, which provide a heat sink, and near the edges of the tumor, leading to a substantial risk of incomplete treatment of the tumor. Given the highly vascular nature of the liver, most large tumors will be in close proximity to at least one major blood vessel.

BRIEF SUMMARY OF THE INVENTION

The present invention provides improved heating of large tumor areas by encircling the tumor with electrodes placed just outside the tumor margin. By heating the tumor "outside in" rather than "inside out" by center placed electrodes, a more uniform temperature gradient can be obtained without excessive electrode temperatures which can lead to loss of electrode effectiveness. Placement of the electrodes outside the tumor creates less risk of tumor seeding, i.e., the spreading cancer cells by the piercing of the tumor tissue with the electrodes. The switching among electrodes prevents shielding effects between the electrodes producing uneven tissue heating. In particular, a "round robin" energizing of opposed electrodes allows the energy to be directed through the center of the tumor.

While the inventors do not wish to be bound by a particular theory, it is believed that increased and early peripheral heading provided by the invention causes a restriction of blood flow to the tumor reducing heat loss through vessels and further promoting tumor cell destruction.

Specifically, then, the present invention provides an electrode array for radiofrequency ablation of a tumor where the array includes a set of elongate electrodes for insertion through tissue of an organ and a holder positioning the electrodes in proximity to each other within a volume of tissue to be ablated. A radiofrequency power supply independently applies electricity to the electrodes in a pattern avoiding simultaneous activation of adjacent electrodes with the same polarity of radiofrequency power to prevent electrostatic shielding effects that reduce the heating between adjacent electrodes having the same polarity of radiofrequency power.

It is thus one object of an embodiment of the invention to permit the use of electrode arrays while promoting even tissue heating by avoiding shielding effects where electrical flow from adjacent electrodes is repelled creating cold spots between the electrodes.

The radiofrequency power supply applies opposite polarity to adjacent electrodes.

It is thus an object of one embodiment of the invention to eliminate shielding problems by promoting piecewise bipolar current flow between the electrodes.

The electrode array may include a ground pad attachable to the patient to provide electrical contact to the patient without substantial heating and the radiofrequency power supply may apply a first polarity to the ground pad and a second polarity to a changing subset of the electrodes, a change in the subset occurring at times independent of a sensed temperature or resistance of the tissue.

It is thus an object of the invention to avoid simultaneous activation of adjacent electrodes with the same polarity in a monopolar configuration.

The holder may provide a series of guides positioning the electrodes with respect to each other to define a ring sized to surround the tumor. In this way, a cylindrical volume of ablated tissue encompassing the tumor may be created.

It is thus one object of at least one embodiment of the invention to provide a system providing reliable and uniform ablation of large tumors.

The holder may be sized so that the electrodes are displaced outside a margin of the tumor so as not to puncture the tumor.

It is thus an object of at least one embodiment of the invention to reduce the possibility of tumor seeding.

It is another object of at least one embodiment of the invention to apply heat at the periphery of the tumor to reduce blood flow to the tumor.

The array may further include a power supply providing radiofrequency power sequentially across opposite ones of the electrodes in the holder, whereby current flow through the tumor center is promoted.

It is thus an object of at least one embodiment of the invention to direct energy through a center of the tumor along multiple spokes of heating to promote a more uniform temperature distribution within the tumor.

The holder may orient the electrodes about their axes and a side of the oriented electrodes in the holder may be insulated.

It is thus another object of at least one embodiment of the invention to allow a sharp temperature gradient at the line of electrodes permitting the electrodes to be placed outside the tumor with reduced damage to non-tumorous tissue.

The electrodes may be insulated along portions of their length.

It is thus another object of at least one embodiment of the invention to provide a controlled height of the ablation as well as area of the ablation to create a controlled ablation volume.

The electrode array may further include a power supply controlling the application of radiofrequency power to the electrodes according to measured change in impedance between the electrodes and tissue.

Thus, it is an object of at least one embodiment of the invention to provide for a feedback mechanism allowing high-powered energy deposition without tissue charring such as may prevent energy absorption by the tissue.

The electrodes may include a means for controlling the electrode insertion with respect to the holder.

It is thus another object of at least one embodiment of the invention to provide a holder that produces a predefined location of tissue ablation relative to the holder.

The circumferential electrode array may have elongate electrodes that are flat blades and the flat blades may be oriented to face a center of the ring.

It is thus another object of at least one embodiment of the invention to preferentially direct the current flow toward the center of the tumor to provide uniform tumor heating.

The invention may offer a kit, including a set of elongated electrodes for insertion through tissue of an organ and a set of holders providing a series of guides positioning the electrodes with respect to each other in a ring, each electrode defining a different ring size to surround different sizes of tumor.

Thus, it is another object of at least one embodiment of the invention to provide for a system that may produce a predefined ablation volume suitable for tumors of different sizes and depths.

These particular objects and advantages may apply to only some embodiments falling within the claims and thus do not define the scope of the invention.

DETAILED DESCRIPTION OF THE PREFERRED EMBODIMENT

I. Partitioning Electrode Array

Figure 1:
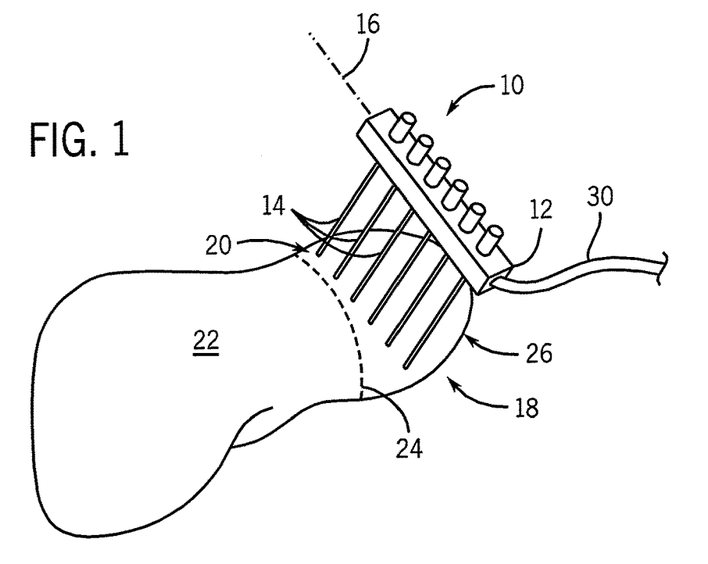
FIG. 1 is a perspective view of a liver showing positioning of the electrode array of a first embodiment of the present invention for insertion into the liver for creating an ablated partition in a first embodiment having fixed electrodes.

Referring now to FIG. 1, an electrode array assembly 10 of a first embodiment of the present invention includes a holder 12 supporting a number of elongate electrodes 14 spaced along an axis 16 to define a generally planar surface 18 among them. The surface 18, for example, may be 8 cm long and 10 cm wide.

Sharpened tips 20 of the elongate electrodes 14 may be inserted into the liver 22 at an insertion line 24 to isolate one lobe 26 of the liver 22 for resection. The elongate electrodes 14 may, for example, be constructed of a biocompatible stainless steel.

The holder 12 may be, for example, an insulating plastic block having holes cut in the holder 12 to receive metallic shafts of the elongate electrodes 14 at regular intervals. In a preferred embodiment, the separation of the electrodes is approximately 1.5 cm. The elongate electrodes 14 may be fixed to the holder 12 so as to be moved in unison for rapid insertion. Each elongate electrode 14 may be independently attached to a separate conductor 23 (not shown in FIG. 2) of a cable 30 providing independently controllable RF power to each of the elongate electrodes 14 as will be described below.

Figure 2:
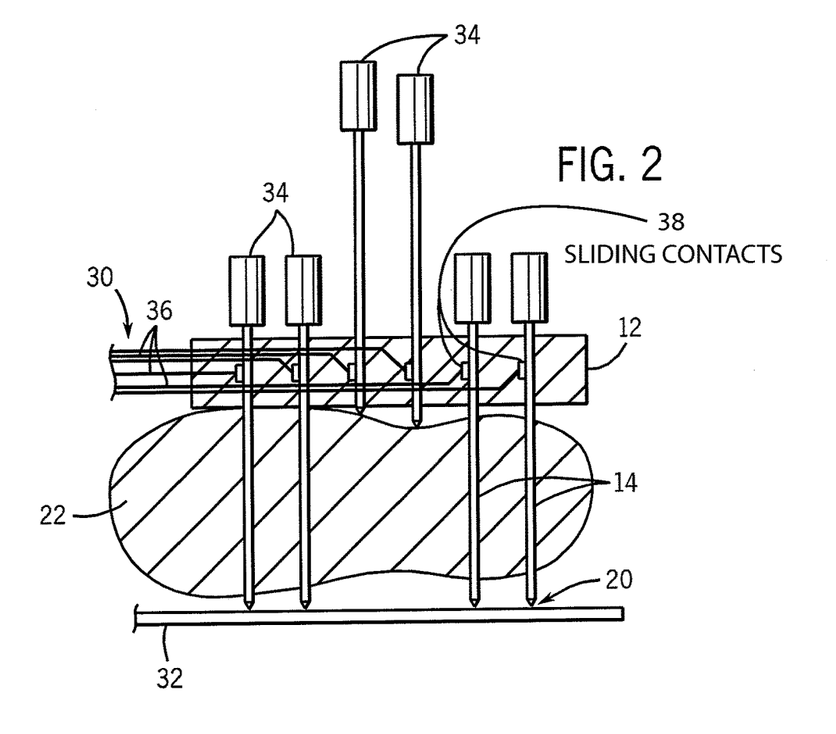
FIG. 2 is a cross-sectional view through the liver after insertion of the electrodes against a stopper plate in a second embodiment having sliding electrodes and electrode connectors.

Referring now to FIG. 2 in an alternative embodiment, each elongate electrode 14 may be separately slidable within the holder 12 as gripped by handles 34 on ends of the elongate electrodes opposite the sharpened tips 20. Separate conductors 36 of the cable 30 may pass to sliding contacts 38 allowing electrical connection to the elongate electrodes 14 throughout their range of travel through the holder 12. In this embodiment, the holder 12 is placed against the liver 22 along insertion line 24 (as shown in FIG. 1) and the individual elongate electrodes 14 are inserted one at a time providing a reduced instantaneous force to be applied to the liver 22. The sliding contacts 38 allow the depth of insertion of the elongate electrodes 14 to be varied freely. A flexible plastic backer sheet 32 may be placed under the liver 22. Insertion of the elongate electrodes 14 through the liver 22 may be stopped by the backer sheet 32 ensuring their full extent through the liver 22 without significant incursion into underlying tissue. In this case, the elongate electrodes 14 may be removable from the holder 12 or may be held in slidable configuration but captive within the holder 12 to prevent the components from being separated.

The backer sheet 32 may also be used with the embodiment of FIG. 1.

Figure 3:
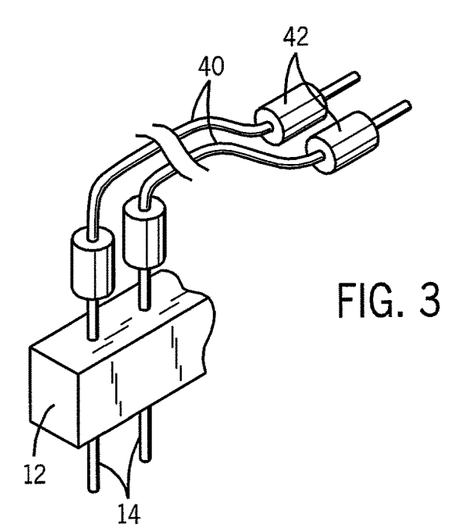
FIG. 3 is a fragmentary view of the holder of the electrodes of FIG. 2 showing an alternative electrical connection method using individual cables attached to each electrode.

Referring now to FIG. 3, the sliding contacts 38 of FIG. 2 may be eliminated in favor of separate cables 40 attached to each elongate electrode 14 and terminating in connectors 42 such as may be connected directly to a source of RF power or to a connector block on the holder 12 (not shown) which may in turn communicate through a cable 30 with the source of RF power. Separate cables 40 may also be used with the embodiment of FIG. 1.

Figure 4:
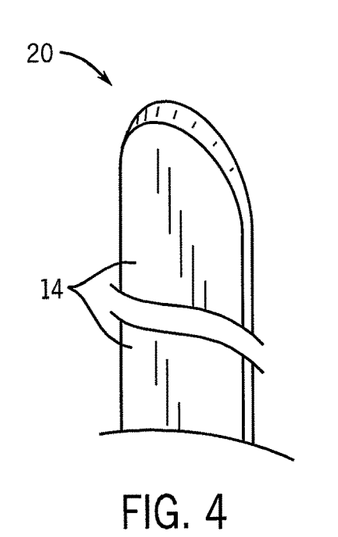
FIG. 4 is a fragmentary detailed perspective view of a sharpened end of one electrode of FIG. 2 showing a blade configuration with a rounded end.

Referring now to FIG. 4, while conventional needle electrodes having a cylindrical cross-section may be used for the elongate electrodes 14 in a preferred embodiment, the elongate electrodes 14 are flattened blades. The tips 20 of the blade elongate electrodes 14 may have a rounded profile with a sharpened peripheral edge to reduce the force of insertion into the liver 22. Alternatively, referring to FIG. 5, the tips 20 of the blade elongate electrodes 14 may have a chisel point leading to a sharpened apex, again with a sharpened peripheral edge. RF power may be applied during insertion of the electrode, to reduce required insertion force and limit bleeding during the insertion.

Figure 5:
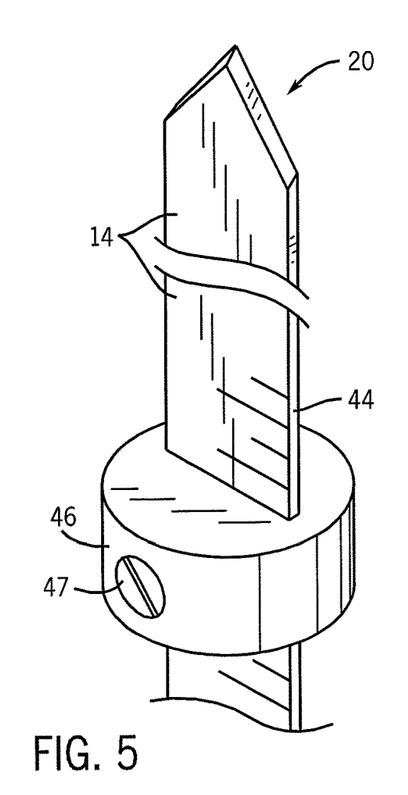
FIG. 5 is a figure similar to that of FIG. 4 showing an alternative embodiment of the blade of FIG. 4 showing a blade configuration with a pointed end and further showing graduation marks on the length of the electrode together with an electrode stop used for controlling insertion depth.

The side of the elongate electrode 14 may include graduations 44 allowing visible control of the depth of the elongate electrode 14. These graduation marks may be used alone or to set a stop 46 using a set screw 47 or the like that attaches to the elongate electrode 14 at any of a range of locations along the side of the elongate electrode 14 so that the depth of the elongate electrode 14 may be reached accurately and quickly.

The handles 34 may be numbered or colored so as to provide for a particular ordering of insertion into the holder 12, in the case when depth has been preset by stops 46, so that the correct elongate electrodes 14 may be inserted appropriately in the holder 12.

Figure 6:
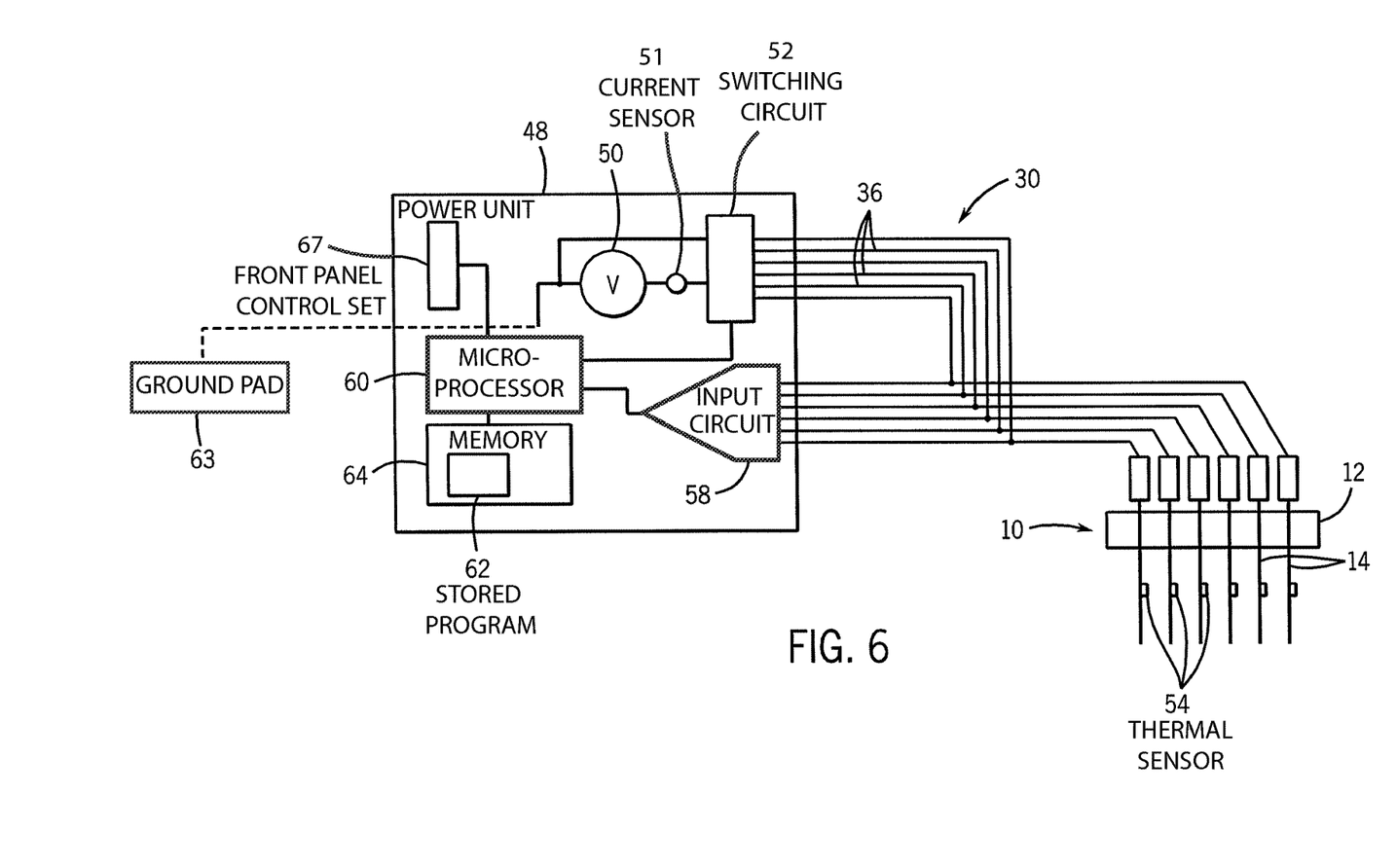
FIG. 6 is a simplified block diagram of a RF power supply suitable for use with the present invention as connected to the electrodes.

Referring now to FIG. 6, the electrode array assembly 10 may be used in conjunction with a power unit 48 providing an RF power source 50. The power unit 48 provides power to the elongate electrodes 14 via an electronically controllable switching circuit 52 communicating with the multiple conductors 36 of cable 30 (or cable 40) passing to the elongate electrodes 14. RF power sources 50 suitable for multiple electrodes are described in U.S. application Ser. No. 10/796,239 filed Mar. 9, 2004 and entitled Multipolar Electrode System for Volumetric Radiofrequency Ablation and U.S. application Ser. No. 10/11,681 filed Jun. 10, 2002 and entitled: Radio-Frequency Ablation System Using Multiple Electrodes, both hereby incorporated by reference.

The power unit 48 may also receive signals from each of the elongate electrodes 14 from an optional thermal sensor 54, such as a thermocouple or solid-state temperature sensor, attached to the surface of the elongate electrodes 14 or within the electrodes. Signals from these thermal sensors 54 may be received by the power unit at input circuit 58 which digitizes and samples the temperature signals and provides them to a microprocessor 60.

The microprocessor 60 executes a stored program 62 held in a memory 64 and also communicates with a front panel control set 67 to provide data to a user and accept user input commands.

While the present invention contemplates that power will be applied to the elongate electrodes 14 in a bipolar mode as will be described, power unit 48 may alternatively communicate with a ground pad 63 to allow monopolar operation.

Figure 7:
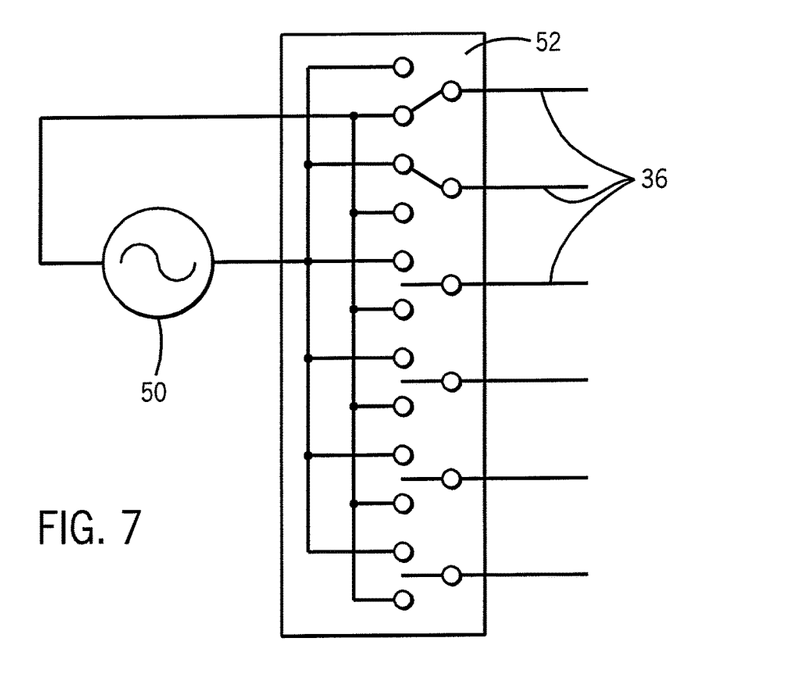
FIG. 7 is a block diagram with a switching circuit used with the power supply of FIG. 6.

Referring now to FIG. 7, the switching circuit 52 provides solid-state switches that allow each conductor 36 attached to an elongate electrode 14 to be switched to either terminal of the RF power source 50 so that the elongate electrode 14 provides either a return or source of RF power. Switching circuit 52 may also be used to disconnect particular ones of the conductors 36 so as to isolate the associated elongate electrode 14 and to allow a duty cycle modulated control of the power going to each elongate electrode 14. Thus, while the power source 50 may optionally run at a constant rate, control of the power may be obtained through the switching circuit 52. The switching circuit 52 is connected to the microprocessor 60 to be controlled thereby.

Figure 8:
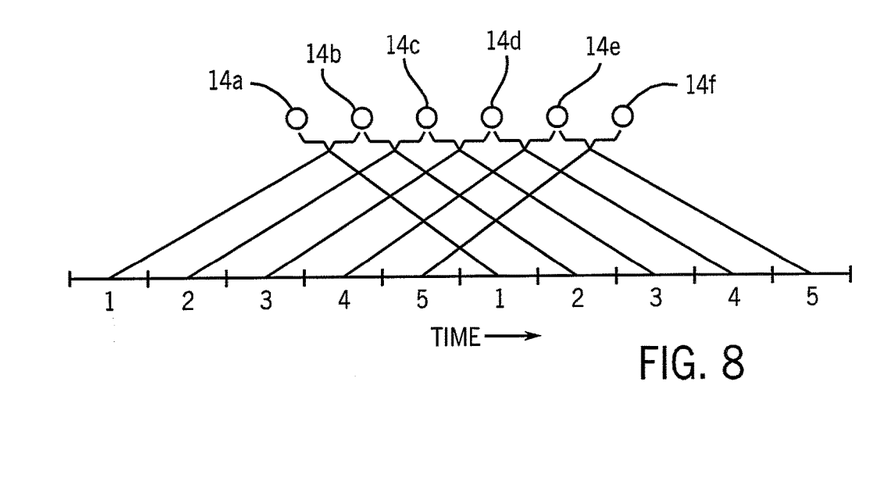
FIG. 8 is a timing diagram showing a sequencing of operation of the switching circuit of FIG. 7 to connect pairs of the electrodes together for bipolar operation.

Referring now to FIG. 8, the microprocessor 60 in a preferred embodiment executes the program 62 in memory 64 to sequentially control the switches of the switching circuit 52 to connect one pair of elongate electrodes 14 to the power source 50 at each time. Accordingly, at a time period 1, a pair of elongate electrodes 14a and 14b will be connected across power source 50 for current to flow therebetween. At this time, all other elongate electrodes 14 are disconnected from the power source 50. At a second time period 2, elongate electrodes 14*b* and 14*c* will be connected across the power source 50 for power to flow therebetween and elongate electrode 14*a* is disconnected from the power source 50.

This process repeats itself for the remaining elongate electrodes 14 until each electrode has been pair-wise connected to the power source 50. After this, the cycle is reinitiated with elongate electrodes 14*a* and 14*b* being connected. This approach may be modified by having multiple pairs of electrodes activated at a time and moved in a similar switching process, the pair separated by in active electrodes.

In an alternative embodiment, one of the elongate electrodes 14 is connected to the power source 50, and all other elongate electrodes 14 are connected to ground providing the return path for the current.

In yet another alternative embodiment, the sequential switching of pairs of elongate electrodes 14 does not proceed continuously from left to right but rather every other sequential pairing is skipped to allow cooling of the tissue near each energized electrode before the next adjacent pair is energized. Accordingly, elongate electrodes 14*a* and 14*b* may be connected across the power source 50 and then elongate electrodes 14*c* and 14*d*, and then elongate electrodes 14*e* and 14*f*, and then elongate electrodes 14*b* and 14*c*, and then elongate electrodes 14*d* and 14*e* and so forth.

As well as limiting the overheating of tissue, the switching of the elongate electrodes 14 provides other benefits. The large number of elongate electrodes 14 may create a very low impedance device which may be beyond the current capability of standard power sources 50. Accordingly, the switched operation also allows that power to be allocated among pairs of the elongate electrodes 14. With standard power sources 50, the ablation region will typically be 1 to 2 cm wide and can be obtained in five to ten minutes. The switching among elongate electrodes 14 may also eliminate shielding effects among electrodes providing a more uniform ablation region. In this shielding effect, the common polarity of adjacent electrodes repels current flow from the other electrode promoting an undesired cool spot between the electrodes.

The amount of power deposited at the tissue surrounding each elongate electrode 14 may be changed by varying the length of the duration of the time periods 1 to 5 as shown in FIG. 8. Alternatively, a high-frequency duty cycle modulation may be imposed on the power applied during the periods 1 to 5 by power source 50 according to well-known techniques.

The control of power deposited at the tissue near each electrode 14 may also be controlled according to the temperature measured at each elongate electrode 14, for example, to reduce power when the temperature rises above a pre-determined threshold either according to a simple thresholding technique or a more complex feedback loop using proportional, integral, and derivative terms.

As an alternative to temperature control, the impedance of the tissue between each pair of electrodes 14 may be determined by monitoring the current flow into the tissue and the particular voltage of the power source 50 (using an in-line current sensor 51), and this impedance can be used to control power by decreasing, or shutting down power for a certain time period as impedance rises, the latter indicating a heating of the tissue.

Impedance measurements can also be used to gauge the thickness of the tissue being ablated. Referring also to FIG. 2, the tissue may have different thicknesses in the slice where the electrode array assembly 10 is inserted. By measuring impedance (with low power application of RF current) between adjacent electrodes 14, the slice thickness along the electrodes 14 can be estimated before ablating the slice. Power applied between each electrode pair can then be applied according to tissue thickness (e.g. tissue twice as thick requires twice the power). In one embodiment, this can be achieved by applying a constant voltage bipolar between each electrode pair. If tissue is twice as thick, impedance is about half as great, and as a result the applied power is twice as high with that constant voltage.

Monitoring current and voltage with the microprocessor 60 may also be used to detect excess or low currents to any particular elongate electrode 14. In the former case, power limiting may be imposed. The latter case may be a sign of a disconnection of one or more elongate electrodes 14 and an indication of this may be provided on the front panel control set 67 to the user.

It will be apparent to those of ordinary skill in the art that a number of other control feedback techniques may be used including those which control current flow or voltage or power (the latter being the product of current and voltage) according to each of these terms.

Figure 13:
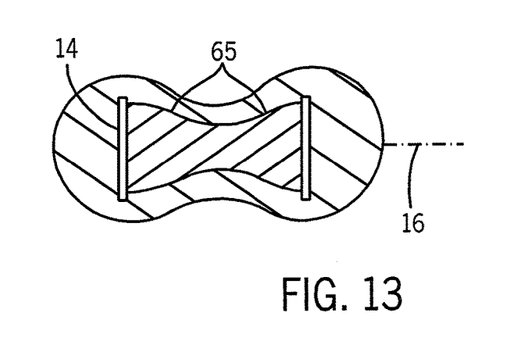
FIG. 13 is a simplified representation of the spacing between two blade electrodes showing the improved ablation zones obtained by the parallel blade structure and bipolar operation.
Figure 14:
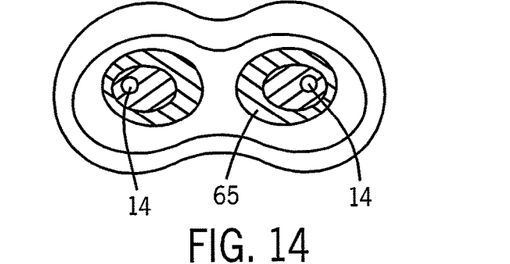
FIG. 14 is a view similar to FIG. 13 showing needle electrodes which can create asymmetrical ablation regions through the use of bipolar stimulation but which may require closer electrode spacing.

Referring now to FIG. 13, the flat shape of the elongate electrodes 14 provides an asymmetrical heating pattern 65 that preferentially ablates tissue along axis 16 allowing increased spacing of elongate electrodes 14 (and thus fewer electrodes and less insertion force) as well as a relatively uniform but thin ablation region. In contrast, the use of needle elongate electrodes 14 as shown in FIG. 14 may require closer spacing to obtain a continuous heating pattern 65.

Figures 9, 10:
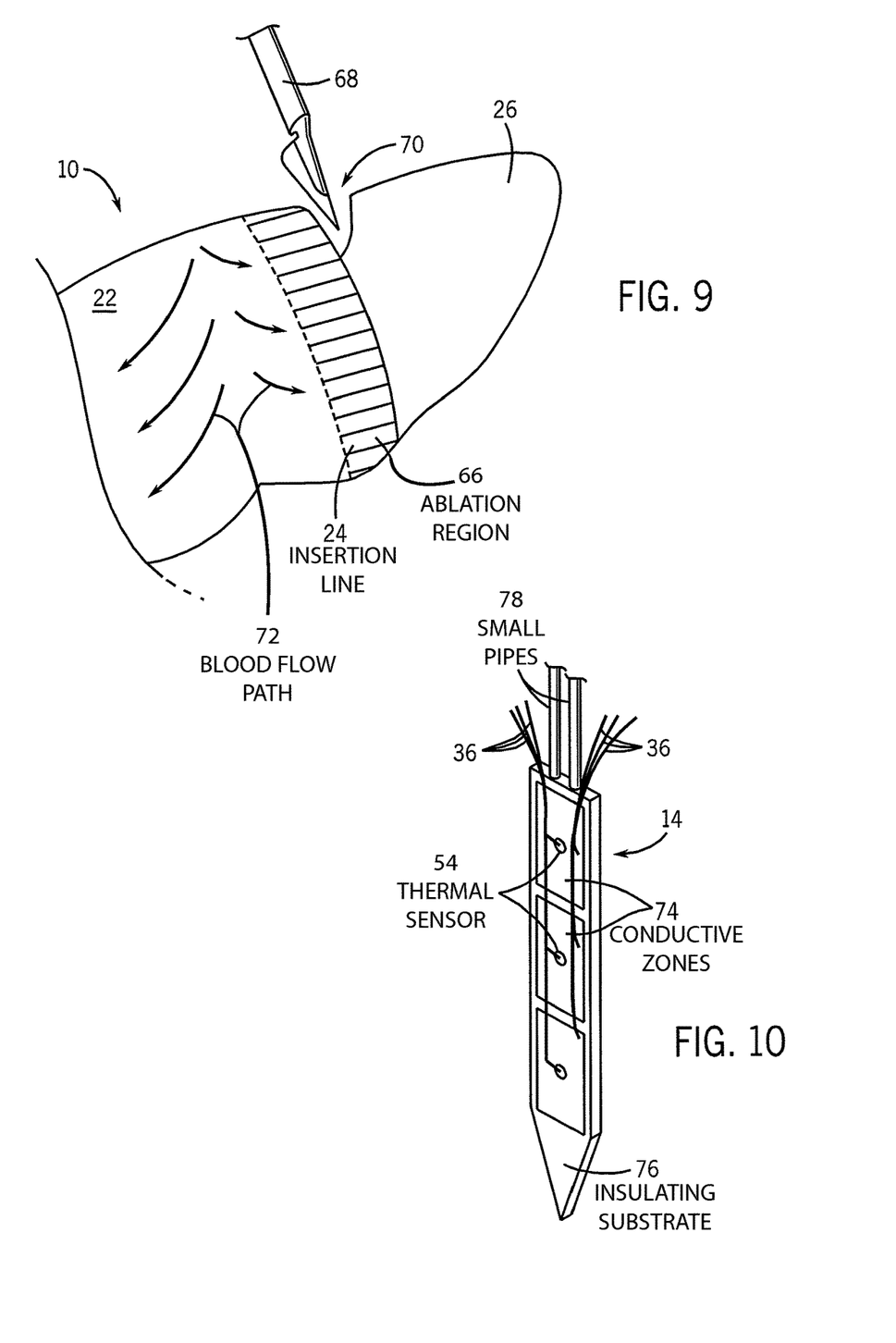
FIG. 9 is a fragmentary perspective view of the liver showing resection of a portion of the tumor after ablation by cutting on an outside edge of the ablation region.
FIG. 10 is an alternative embodiment of the electrode of FIG. 5 having multiple isolated conductive zones and thermal sensors on each zone for independent control of ablation along the length of the electrode.

Referring now to FIG. 9, once the liver 22 is ablated along an ablation region 66 intersecting insertion line 24, a scalpel 68 may be used to resect a lobe 26 of the liver 22 by making a cut 70 on the outside of the ablation region 66 with respect to a general path 72 of blood flow through the liver 22. The ablation region 66 thus reduces blood loss during the resection process.

Referring now to FIG. 10 in an alternative embodiment, elongate electrode 14 may include a number of independently conductive zones 74 separated on an insulating substrate 76. Each conductive zone 74 communicates with a separate conductor 36 so as to allow independent control of current flow into the tissue not simply among elongate electrodes 14 but along the length of each elongate electrode 14. A thermal sensor 54 may be associated with each region further providing independent feedback control of each region.

Referring still to FIG. 10, active cooling of the elongate electrodes 14 may also be accomplished through the use of small pipes 78 through which cooled fluid such as gas or liquid may be passed.

Figure 11:
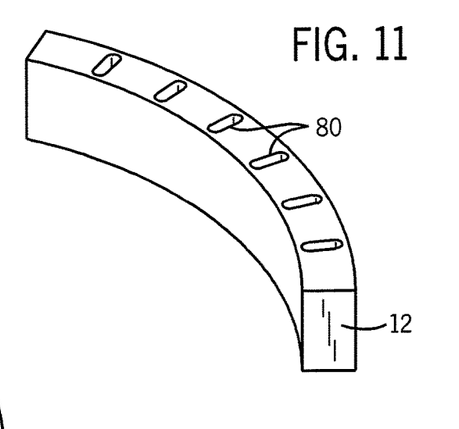
FIG. 11 is an alternative embodiment of the holder of FIG. 1 for providing a curved surface for the ablation region.

Referring now to FIG. 11 in an alternative embodiment, the holder 12 is not planar, but may have an arcuate shape with holes 80, through which the elongate electrodes 14 are inserted, being arranged along a radius so that the elongate electrodes 14 as positioned by the holder 12 describe a hemi cylindrical surface conforming to an outline, for example, of a tumor in the lobe 26 to be resected.

Figure 12:
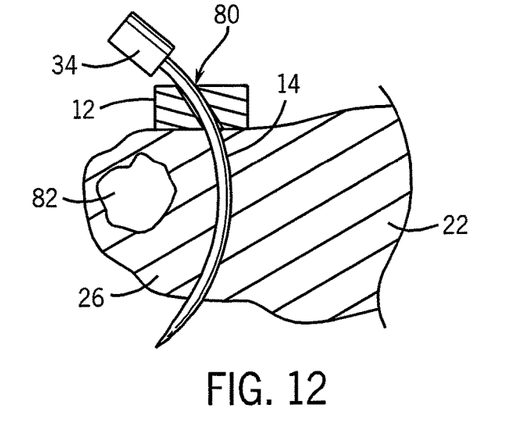
FIG. 12 is a cross-sectional view through a liver showing the use of a curved electrode such as may be used with the curved holder FIG. 11 to realize a hemispherical ablation surface or with the straight holder of FIG. 1 to realize a cylindrical ablation surface.

Referring to FIG. 12, alternatively or in addition, each elongate electrode 14 may be curved so as to fit through an arcuate hole 80 in the holder 12, the holder 12 which may be straight or curved. In the former case, the elongate electrodes provide a hemicylindrical ablation surface having an axis parallel to axis 16 along which the elongate electrodes are separated. In the latter case, the elongate electrodes provide a curved surface in two dimensions approximating a hemispherical surface to conform to a possible tumor region 82 within the lobe 26.

The present invention is not limited to use with the liver 22, but may be used generally in any medical procedure where a barrier needs to be created prior to a cutting of tissue and in particular for surgery in other organs. The switching schedule through which power deposition is controlled may be regular or varied.

II. Ablating Electrode Array

Figure 15:
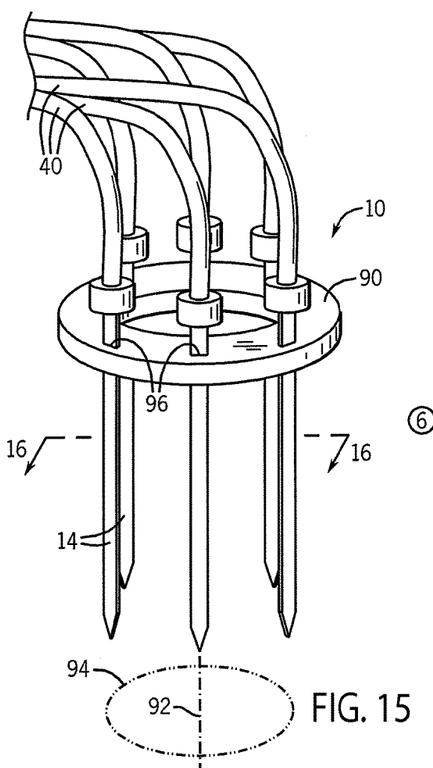
FIG. 15 is an elevational perspective view of an alternative embodiment of the invention providing for a ring of electrodes for ablation of a tumor.

Referring to FIG. 15, an alternative embodiment of the electrode array assembly 10 provides for the improved ablation of tumors and employs a ring electrode holder 90. The ring electrode holder 90 supports a set of electrodes 14 distributed about the ring and extending perpendicularly to the plane of the ring. Generally, each of the electrodes 14 is spaced at equal angles about a central axis 92 to define a ring area 94 therebetween.

Figure 16:
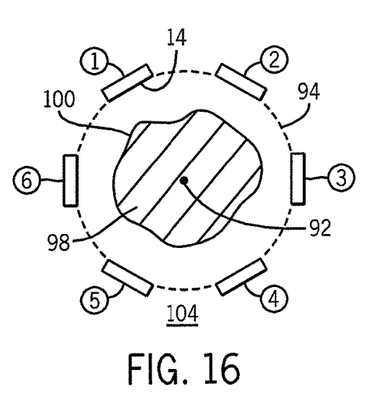
FIG. 16 is a plan cross-sectional view along lines 16-16 of FIG. 15 showing a tumor surrounded by the electrodes of FIG. 15 and further showing the axial orientation of the electrode blades.

Referring also to FIG. 16, the ring area 94 is ideally sized so that the electrodes 14 may surround a tumor 98 intersected by the central axis with each electrode positioned to lie slightly outside of a margin 100 of the tumor 98, for example, by approximately 1 cm.

The electrodes 14 may slide within a set of slots 96 cut through the electrode holder 90 so that the electrodes 14 may be installed one at a time to reduce the instantaneous force required to install the electrode array assembly 10 on the patient. The holder 90 is preferably insulting material to prevent current flow therethrough among the electrodes 14 and may, for example, include an adhesive or the like on one surface to help position it against the patient's skin.

The slots 96 may be keyed to accept only specific pairs of the electrodes to orient the electrodes in a particular pattern for energization as will be described below. Such keying, for example, may make use of wards or other mechanical features or may be visual markings, such as color, or the like to enforce correct electrode placement. Alternatively, electrode contacts may be incorporated into the ring as described above with respect to FIG. 2 to ensure a particular electrical connection pattern is realized.

As shown, the electrode holder 90 is circular with a central opening but any closed shape may be used so long as the electrodes 14 can be positioned to surround a tumor 98. The central opening of the electrode holder is not necessary.

As shown in FIG. 16, the electrodes 14 may be blades as described above, with respect to FIGS. 13 and 14 with their broad surfaces following the edge of the ring area 94. Preferably the electrodes 14 are arranged in pairs opposed across the axis 92 so that normals to the broad surfaces of the blades of the opposed electrodes 14 lie on a single line passing through the axis 92 and the center of the tumor 98. Thus for example, electrodes (3) and (6) form one pair positioned about the tumor 98 at angles 0 degrees and 180 degrees, respectively. Likewise electrodes (2) and (5) form a pair positioned about the tumor 98 at angles 60 degrees and 240 degrees, respectively and electrodes (1) and (4) form one pair positioned about the tumor 98 at angles 120 degrees and 300 degrees, respectively. As will be described below, the electrodes are can be energized pair by pair to provide improved heating uniformity of the tumor 98.

Figure 17A:
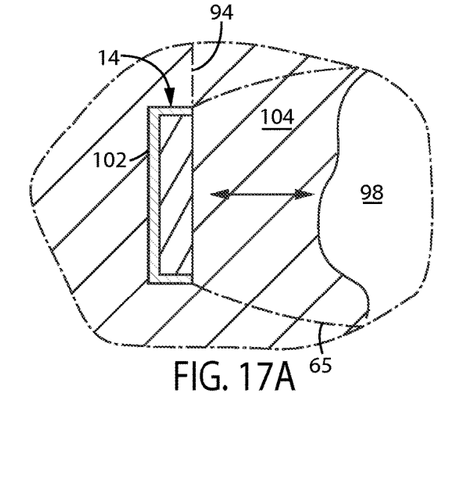
FIGS. 17a and 17b are detailed, fragmentary, plan, cross sectional views of an electrode of FIG. 16 showing two alternative embodiments providing insulation of a surface of the electrode facing away from the tumor.
Figure 17B:
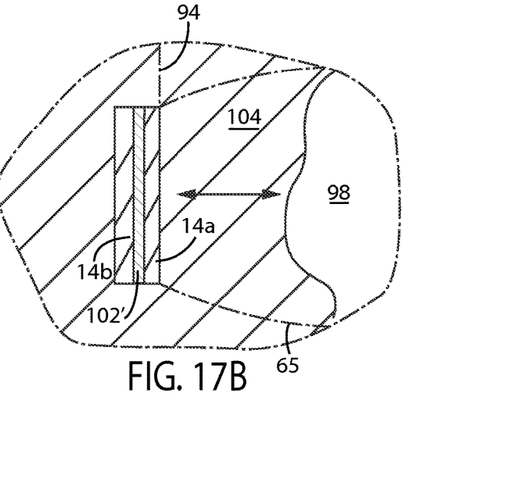

Referring now to FIGS. 16 and 17*a*, each electrode 14 may have an outer electrically and thermally insulating coating 102 applied to a side of the electrode 14 away from the tumor 98 so as to reduce electrical and thermal conduction and hence heating of tissue outside of the ring area 94. In the case of blade electrodes 14, the insulating coating 102 may cover three sides of the cross section of the electrode 14 and may, for example, be a biocompatible material, such as Teflon. Alternatively, referring to FIGS. 16 and 17*b*, a sandwich construction may be adopted where the insulating layer 102' is placed between two metallic blade electrodes 14*a* and 14*b*, with electrode 14*a* closest to the tumor electrically connected to a power source and electrode 14*b* not connected to a power source, insulated from 14*a* by layer 102' and providing only stiffness and resilience.

Figure 18:
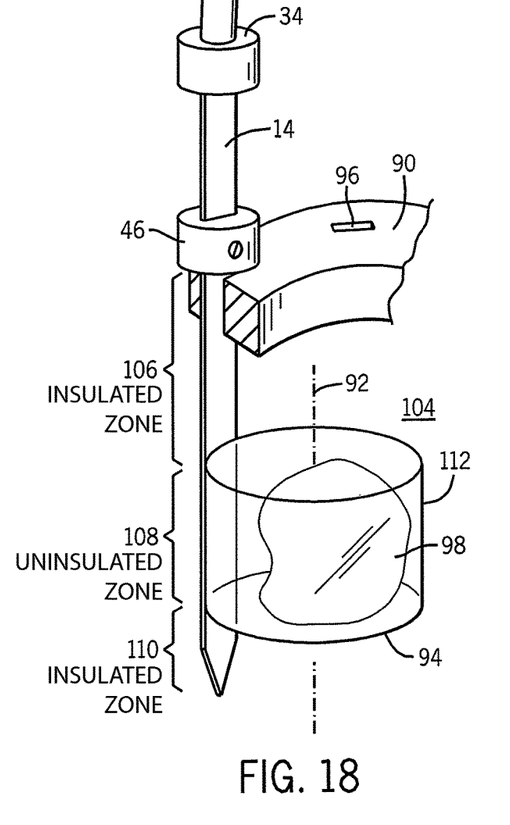
FIG. 18 is a fragmentary perspective view of the electrode ring of FIG. 15 in an alternative embodiment including stops for controlling the depths of the electrodes and insulation of portions of the length of the electrodes to control the height of the ablated volume.

Referring now to FIG. 18, each electrode 14 may have an upper handle 34 that may be grasped by a physician to position the electrode 14 and that may provide a connector to a power supply cable 40. The electrodes 14 may each also include a sliding stop 46 as described previously, the stop adjustably affixed to a portion of the electrode 14 on the opposite side of electrode holder 90 from the patient to abut the upper surface of the holder 90 to thereby control the insertion depth of the electrode 14.

The length of each electrode 14 extending into the tissue 104 of the patient may be further electrically insulated to create three zones 106, 108 and 110, along the length of the electrode 14, with zone 106 closest to the holder 90 and zone 110 furthest from the holder 90, and zone 108 positioned in between. The electrodes 14 at zones 106 and 110 may be wholly insulated on their outer surfaces within those zones to prevent heating of the tissue in those zones so as to limit the region of ablation to zone 108 and in this way creating an ablation cylinder 112 having a base defined by the ring area 94 and a height and location defined by the height and location of zone 108. Generally, zone 110 will be minimized so as to prevent unnecessary insertion of the electrode 14 into the patient.

Figure 19A:
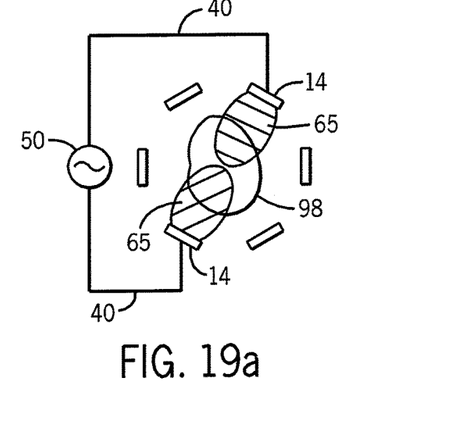
FIGS. 19a-19d are simplified representations of the tumor and pairs of the electrodes of FIG. 16 showing an activation pattern of the electrodes.
Figure 19B:
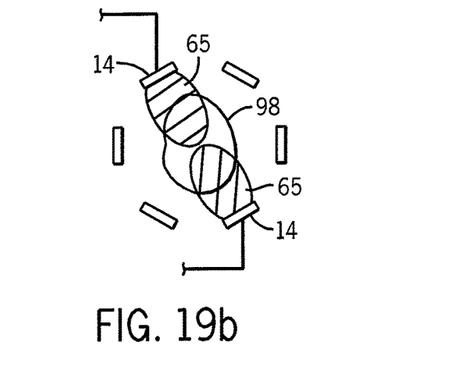
Figure 19C:
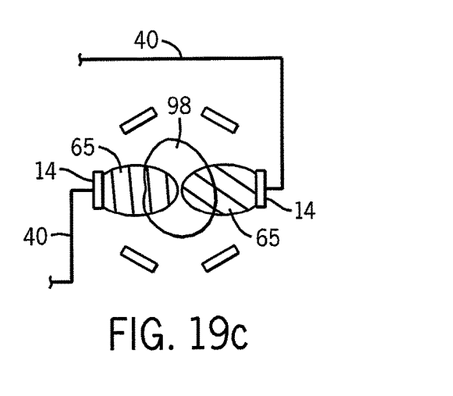
Figure 19D:
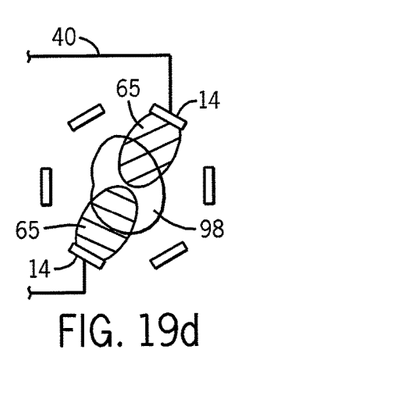

Referring now to FIGS. 16 and 19*a*, the electrodes 14 are preferably energized in a round robin pattern by a radiofrequency power source switched by an appropriate switching system, for example, as described above with respect to FIG. 7. In this pattern, opposite electrodes 14 are connected one pair at a time to conduct electricity therebetween through the tumor 98. Thus, for example, as shown in FIG. 19*a*, electrodes (2) and (5) may be connected to the RF source 50 positioned opposite the tumor 98 to create a heating pattern 65 extending approximately 45 degrees clockwise from vertical (as depicted). At this time, the other electrodes 14 may remain electrically neutral, e.g., in a high impedance state to minimize shielding or other undesired distortion of the heating pattern 65 and to allow cooling recovery of the tissue immediately adjacent to the electrodes 14 to prevent local charring. A short period of time later, for example, 150 milliseconds later, electrodes (2) and (5) may be disconnected and electrodes (1) and (4) connected to the RF power source 50 to create a heating pattern 65 extending generally 45 degrees counterclockwise to vertical, passing through the tumor 98. 150 milliseconds later, as shown in FIG. 19*c*, electrodes (6) and (3) may be connected to the RF power source 50 to create a generally horizontal heating pattern 65 through the tumor. Finally, 150 milliseconds later, electrodes (2) and (5) may be reconnected as shown in FIG. 19*a* to repeat this pattern. This switching pattern provides a composite heating centered on the tumor 98.

Figure 20:
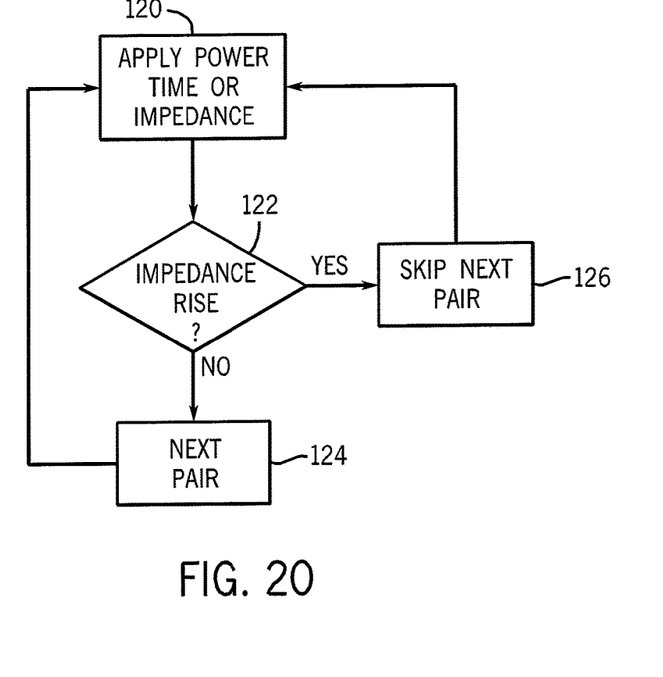
FIG. 20 is a flow chart showing a control loop for further modifying the activation pattern of FIG. 19 with respect to measured impedance.

The period of time allotted to each pair or electrodes 14 may be adjusted in a closed loop control strategy according to measured electrode temperature, impedance or other similar value, to prevent charring at the electrodes 14 such as may ultimately reduce the ability to transfer electrical power into the tissue. Alternatively, as shown in FIG. 20, the sequence of the energized pairs of electrodes 14, described above with respect to FIGS. 19*a*-19*d*, may be modified based on measurement of the impedance (and/or temperature) of the interface between the electrode 14 and the tissue 104, the former deduced by a measurement of the voltage across the electrodes and the current flow therethrough, and the latter measured with a thermocouple or the like attached to the electrode 14.

At a first step in this control strategy, as may be implemented by microprocessor 60, described above with respect to FIG. 6, and indicated by process block 120, power is applied to a given pair of electrodes for a given time or until an impedance limit is reached (e.g., 50 ohms), whichever is sooner. At decision block 122, historical data of the impedance rise on the next pair of electrodes in the sequence is reviewed to determine whether the impedance rise over a desired threshold (which may be the same or different from the threshold of process block 120) has occurred in the last 10 seconds or other pre-determined time. If not, then as indicated by process block 124, the next electrode pair is connected to the power supply and power is applied per process block 120. On the other hand, if the impedance has risen past the threshold of block 120 in the last 10 seconds, what would normally be the next pair of electrodes is skipped per process block 126 to allow further cooling of those electrodes 14. Other control strategies may also be used including voltage or current control and duty cycle modulation of the individual on-times of each electrode.

Figure 21A:
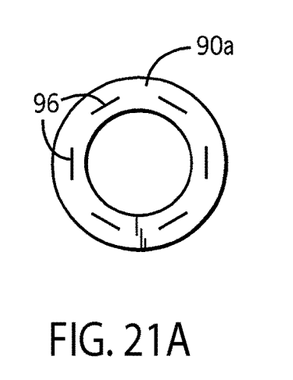
FIGS. 21a, 21b and 21c are top plan views of a set of electrode holder rings that, along with electrodes, may form a kit to be used for tumors of different sizes.
Figure 21B:
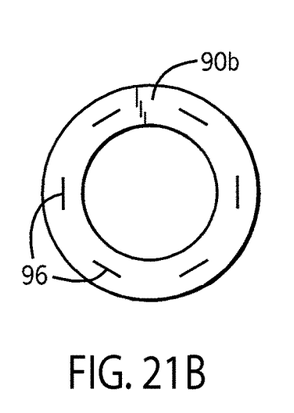
Figure 21C:
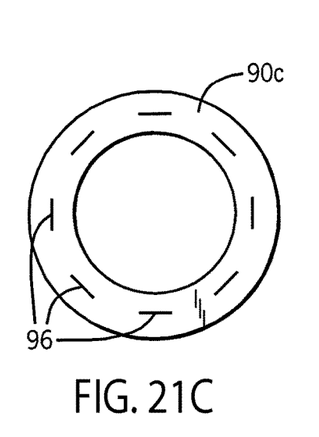

Referring now to FIGS. 21a, 21b and 21c, the present invention may provide a kit of holders 90a, 90b and 90c, each having slots 96, defining rings of different diameters, shapes and numbers of electrodes 14. Those with larger rings, for example, holder 90c, may provide additional slots 96 for additional electrodes. The physician may select a particular ring depending on the size of the tumor and its projected diameter along the direction of insertion of the electrodes, and then fit the electrodes into the ring during the procedure. A collection of different electrode sets each having different heights of the uninsulated zone 108 may provide similar control of the height of the treatment zone.

While the holder 90 described above may be a simple insulated ring, the present inventors also contemplate the possibility of more complex holding devices including those that allow adjustability in the ring diameter, for example by articulated components, and those adapted to machine assisted or robotic placement.

It is specifically intended that the present invention not be limited to the embodiments and illustrations contained herein, but include modified forms of those embodiments including portions of the embodiments and combinations of elements of different embodiments as come within the scope of the following claims.

We claim:

1. An electrode array for radiofrequency ablation of a tumor having a diameter, the electrode array comprising:
    a set of elongate electrodes for insertion through tissue of an organ wherein the elongate electrodes are adapted to extend through tissue along straight lines;
    a holder having guides slidably receiving independently slidable individual elongate electrodes in parallel fashion, the guides displaced in a ring having a diameter greater than the tumor diameter, the holder adapted to position the individual elongate electrodes for extension perpendicular to a plane of the ring in proximity to each other and to surround the tumor to be ablated; and
    a radiofrequency power supply independently applying electricity to the electrodes in a changing on and off pattern according to a predetermined time schedule and avoiding simultaneous activation of adjacent electrodes with the same polarity of radiofrequency power wherein the radiofrequency power supply sequentially switches on opposite ones of the electrodes in the holder, whereby current flow through a tumor center is promoted;
    wherein the electrodes have a rectangular cross section and wherein the holder is adapted to position a broadest face of the rectangular cross section, being a largest dimension of the rectangular cross section, oriented to face a center of the ring and a normal of the broadest face passing through a center of the ring, to surround the tumor in the organ when extended through tissue.

2. The electrode array of claim 1 wherein the radiofrequency power supply applies opposite polarity to adjacent electrodes.

3. The electrode array of claim 1 wherein the radiofrequency power supply further controls application of radiofrequency power to the electrodes according to measured changes in impedance or temperature between the electrodes and tissue according to impedance or temperature readings produced by a sensor and delivered to a microprocessor.

4. The electrode array of claim 1 wherein the electrodes include a means for controlling the electrode's insertion depth with respect to the holder.

5. The electrode array of claim 1 further including additional holders providing a kit of holders, each holder providing guides displaced along a ring of different diameter, each holder alternatively receiving the set of elongate electrodes.

6. The electrode array of claim 5 wherein the kit of holders provides holders having a different number of guides for receiving a different number of elongate electrodes.

7. The electrode array of claim 5 wherein the kit of holders provides holders having the same number of guides for receiving a same number of elongate electrodes.

8. The electrode array of claim 5 wherein the kit of holders provides holders with guides displaced along rings of different diameters where the diameter is adjustable by fitting the elongate electrodes into different of the holders.

9. The electrode array of claim 1 wherein each electrode is separately removable from the guides of the holder.

10. The electrode array of claim 1 wherein each electrode has a handle on an end of the electrode opposite an insertion end and adapted to be grasped by a physician to position the electrode.

11. The electrode array of claim 1 wherein the guides receive the electrodes evenly spaced around the ring.

12. The electrode array of claim 1 wherein the guides are slots guiding the electrodes along an insertion axis.

13. The electrode array of claim 1 wherein the holder is insulated.

14. The electrode array of claim 13 wherein the holder includes an adhesive on an outer surface of the holder positioned to adhere to skin of a patient during insertion of the electrodes.

15. The electrode array of claim 1 wherein the holder is a ring having a central opening.

16. The electrode array of claim 1 wherein the electrodes are flattened blades.

17. The electrode array of claim 16 wherein an insertion end of the electrodes has a chiseled point and a sharpened apex.

18. The electrode array of claim 1 wherein the electrodes have graduations marks indicating an insertion depth.

* * * * *